United States Patent [19]

Herring

[11] Patent Number: 5,518,929

[45] Date of Patent: May 21, 1996

[54] METHOD OF MAKING A BLOOD GAS/ELECTROLYTE CONTROL

[75] Inventor: Kathryn D. Herring, Miami, Fla.

[73] Assignee: Dade International Inc., Deerfield, Ill.

[21] Appl. No.: 403,092

[22] Filed: Mar. 13, 1995

Related U.S. Application Data

[63] Continuation of Ser. No. 252,383, Jun. 1, 1994, Pat. No. 5,422,278, which is a continuation of Ser. No. 4,211, Jan. 13, 1993, abandoned, which is a continuation of Ser. No. 794,693, Nov. 18, 1991, abandoned, which is a continuation of Ser. No. 628,990, Dec. 17, 1990, abandoned, which is a continuation of Ser. No. 511,824, Apr. 16, 1990, abandoned, which is a continuation of Ser. No. 361,836, Jun. 1, 1989, abandoned, which is a continuation of Ser. No. 121,499, Nov. 17, 1987, abandoned.

[51] Int. Cl.$^6$ ............................................. G01N 31/00
[52] U.S. Cl. ................................ 436/11; 436/8; 436/10; 436/16; 436/68; 436/74; 436/79; 436/174; 252/408.1
[58] Field of Search ............................ 436/8–19, 68, 436/74, 79, 125, 127, 145, 146, 174; 252/408.1

[56] References Cited

U.S. PATENT DOCUMENTS

| | | | |
|---|---|---|---|
| 3,681,255 | 8/1972 | Wilfore et al. | 436/11 |
| 3,859,049 | 1/1975 | Ware et al. | 436/11 |
| 3,973,913 | 8/1976 | Louderback | 436/11 |
| 4,019,861 | 4/1977 | Dahms | 436/45 |
| 4,126,575 | 11/1978 | Louderback | 436/11 |
| 4,163,734 | 8/1979 | Sorensen et al. | 436/11 |
| 4,231,869 | 11/1980 | Carlberg et al. | 210/763 |
| 4,279,775 | 7/1981 | Louderback et al. | 436/11 |
| 4,299,728 | 11/1981 | Cormier et al. | 436/11 |
| 4,369,127 | 1/1983 | Cormier et al. | 436/11 |
| 4,375,743 | 3/1983 | Sullivan | 53/434 |
| 4,458,021 | 7/1984 | Herring | 436/11 |
| 4,469,792 | 9/1984 | Simmonds et al. | 436/11 |
| 4,485,174 | 11/1984 | Chiang et al. | 436/11 |
| 4,643,976 | 2/1987 | Hoskins | 436/15 |
| 4,678,754 | 7/1987 | Hoskins | 436/11 |
| 4,753,888 | 6/1988 | Chiang | 436/11 |
| 4,806,486 | 2/1989 | Sprokholt et al. | 436/19 |

FOREIGN PATENT DOCUMENTS

| | | |
|---|---|---|
| 0213343 | 3/1987 | European Pat. Off. . |
| 8706343 | 4/1986 | WIPO . |

OTHER PUBLICATIONS

Diamond Sensor Systems–Brochure with Declaration of Steven Enzer.
Confitest II–Aqueous Blood Gas Control.
Covington, "Standard Reference Solutions for Blood Electrolyte Determinations", iFee Workshop, Oslo, 1983.
D'Orazio, "The Effects of Hepes and MOPS Zwitterionic Buffers on the Activities of Sodium and Potassium in Multi–ISE Calibrating Solutions and Their Contribution to the Residual Liquid Junchon Potential" at Open Kel Junctions, Int'l Symposium on the Measurement of Blood Electrolytes, Danvers, MA, Sep. 23–25, 1987.
"Direct Potentiometric Measurements in Blood," Proceedings of the Workshop on Direct Potentiometric Measurements in Blood, National Bureau of Standards, Gaitherburg, MD, May 18–20, 1983, pp. 89–91.
"Feasibility Test of Proposed Calibration Solution on Commercial ISE Instruments", iFee Workshop, Helsinki, 1985.
Oswald et al., "Calibration Standards for Multi–Ion Analysis in Whole Blood Samples", Progress in Enzyme and Ion–Selective Electrodes, Berlin: Springer, pp. 74–78 (1981).

*Primary Examiner*—Jill Warden
*Assistant Examiner*—Maureen M. Wallenhorst
*Attorney, Agent, or Firm*—Lois K. Winston; Cynthia G. Tymeson

[57] ABSTRACT

Aqueous solutions containing buffers and electrolytes are adjusted to levels required for calibration of both blood gas analyzers and ion selective electrolyte analyzers. A control material, composed of similar matrix, is adjusted to three levels of blood gas and electrolyte conditions. These quality control materials are used to monitor blood gas/electrolyte laboratory instrumentation.

8 Claims, No Drawings

METHOD OF MAKING A BLOOD GAS/ELECTROLYTE CONTROL

This is a continuation of application Ser. No. 08/252,383, filed Jun. 1, 1994, and now U.S. Pat. No. 5,422,278 issued Jun. 6, 1995, which is a continuation of application Ser. No. 08/004,211, filed Jan. 13, 1993, and now abandoned, which is a continuation of application Ser. No. 07/794,693, filed on Nov. 18, 1991, now abandoned which is a continuation of application Ser. No. 07/628,990, filed on Dec. 17, 1990, now abandoned, which is a continuation of application Ser. No. 07/511,824, filed on Apr. 16, 1990, now abandoned, which is a continuation of application Ser. No. 07/361,836, filed on June 1, 1989, now abandoned, which is a continuation of Ser. No. 07/121,499, filed on Nov. 17, 1987, now abandoned.

FIELD OF THE INVENTION

This invention relates to aqueous solutions containing buffers and electrolytes adjusted to specific levels for calibration or quality control of chemical analyzers. In particular, this invention relates to a solution which has the specific parameters for the calibration and quality control of both blood gas and ion selective electrode instrumentation.

BACKGROUND OF THE INVENTION

Analytical devices capable of determining various parameters in whole blood with the aid of ion-selective electrodes have been used in intensive care units and in the field of anaesthetics. Blood gases, such as carbon dioxide and oxygen, can be measured using ion selective electrodes. An ion selective electrode consists of an electrochemical half-cell (an internal electrolyte solution and an internal reference electrode) and a sensing membrane. These types of electrodes are used to measure one type of ion in the presence of other ions in the bodily fluids. To obtain accurate measurements, a set of calibration solutions are used to calibrate the electrodes.

In addition to calibration, the tests run on clinical chemical analyzers are verified by specific control solutions. Under ideal conditions, control materials used in the verification of instrumentation performance should have essentially the same constituents as those present in the fluid which is to be subjected to analysis.

Most blood gas instruments are currently calibrated using a buffer for the pH and humidified gases for carbon dioxide and oxygen. Some instruments tonometer buffer inside the instrument and use this liquid for equilibration. Blood gas instruments that also measure electrolytes have separate solutions for calibration and control of the ion selective electrodes. The electrolyte calibrator and control solutions do not currently contain all the blood gas parameters.

BRIEF SUMMARY OF THE INVENTION

The present invention relates to calibrating and control solutions for instrumentation which measures both blood gas and electrolytes and a method of using such solutions with blood gas instruments. This invention relates to aqueous solutions containing buffers and electrolytes adjusted to specific levels for calibration or quality control blood gas instruments. In particular, the present invention relates to a novel blood gas-electrolyte instrument control solution having three levels. The three levels simulate three different patient conditions: one normal and two abnormal. Level one has low electrolyte parameters, acidosis pH and gas parameters which represent respiratory acidosis, i.e. low $O_2$ and high $CO_2$ concentrations. Level two has normal conditions in all parameters. Level three has high electrolyte parameters, alkalosis pH, and gas parameters which represent respiratory alkalosis, i.e. low $CO_2$ and high $O_2$ concentrations.

Additionally, the present invention relates to a novel blood gas electrolyte instrument calibrating solution that contains parameters necessary for the calibration of both blood gas and ion selective electrode instrumentation. In particular, the present calibrating solution contains two levels having the necessary parameters. Level one has normal pH, $pCO_2$ and $pO_2$ and electrolytes. Level two is the zero oxygen calibrator. It has physiologically high concentrations of $CO_2$, physiologically low electrolyte levels and zero $O_2$.

DESCRIPTION OF THE PREFERRED EMBODIMENTS

The blood gas-electrolyte calibrating solutions of this invention are prepared by conventional manufacturing techniques using readily available materials. A typical calibrating solution with the contemplation of this invention is prepared by simply combining in appropriate relative proportions buffer, electrolytes, and other standard auxiliary reagents.

EXAMPLE I

A Diamond Sensor System GEM 6 Blood Gas Electrolyte monitor is calibrated with a calibrating solution having two levels. The calibrating solution is comprised of an aqueous biological buffer with a preservative, electrolytes, and blood gas components. A detergent is added for use as a wetting agent.

Level one has normal pH, $pCO_2$, $pO_2$. Sulfate ions are used to keep the calcium in solution. Level two is the "O" calibrator. It has low pH, physiologically high concentrations of $CO_2$ and zero $O_2$ and physiologically low electrolyte levels. The $O_2$ is kept at zero, even in the presence of room air, with sufficient sulfite and nitrogen.

TABLE I

|  | LEVEL 1 | LEVEL 2 |
|---|---|---|
| NaCL (mMol/L) | — | 46 |
| $CaCl_2$ (mMol/L) | 3.8 | 0.3 |
| KCL (mMol/L) | 6.9 | 2.2 |
| Sulfite (mMol/L) | — | 40 |
| Sulfate (mMol/L) | 26 | — |
| $CO_2$ (mmHg) | 35 | 65 |
| $O_2$ (mmHg) | 115–170 | 0 |
| MOPS (mMol/L) | 100 | 100 |
| pH (37° C.) | 7.4 | 6.9 |
| $Na^+$ (mMol/L) | 135 | 150 |
| $K^+$ (mMol/L) | 6.0 | 2 |
| $Ca^{2+}$ (mMol/L) | 2.0 | 0.2 |
| $CL^-$ (mMol/L) | 120 | 80 |
| Ionic Strength mMol/L | 160 | 160 |

Table I lists the composition of the two levels of the blood gas electrolyte calibrating solution together with concentrations and pH values. The pH of the solution is adjusted and sodium bicarbonate is added to reach the desired carbon dioxide level. Albumin may be added if a protein matrix is desired.

The electrolytes used in this control solution may be: sodium, potassium, calicum, and chloride. Lithium is not added to the calibrating solutions or controls for the DSS GEM 6 instrument due to interference with the sensors, although, with other instruments lithium may be used. The buffer used is designed to give the appropriate pH value by combining the acid and salt forms. This buffer was selected due to the very small temperature effect demonstrated by the buffer. Various solutions having the above discussed levels can be prepared for as many calibration points as necessary for the instrumentation. Most instrumentation use a one or two point calibration for sloping electrodes.

The final solution is sterile filtered and is stored in gas tight containers without a gaseous headspace. In the final container no further equilibrium with gases will take place and the final solution is therefore not affected by pressure and temperature.

The addition of calcium as an electrolyte and bicarbonate as a buffer for pH and carbon dioxide, creates conditions for the formation of calcium carbonate. Calcium carbonate is an insoluble precipitate, which will eventually remove all the calcium from solution and therefore make the calcium no longer measurable as an ion. To prevent this from occurring sulfate ions are added which protect the calcium ion from contact with the carbonate ion. This protection is necessary when high levels of both calcium and carbon dioxide are desired.

The level I solution is tonometered with 100% nitrogen until the oxygen level is less than 10 mmHg. Sulfite ions are then added to scavenge the remaining oxygen. The sulfite is added in excess so that residual sulfite is available to scavenge oxygen that may contact the solution. This enables the solution to maintain a zero oxygen value. The bicarbonate is then added to create the desired $pCO_2$ value.

The solutions are then tonometered using the appropriate gases needed to reach the requested oxygen and carbon dioxide values (the final solutions are sterile filtered and stored in gas tight containers without headspace). No further equilibrium with gases takes place and the final solution is not affected by pressure and temperature. The solution is stable in the final container and is ready for use with a blood gas/electrolyte analyzer.

EXAMPLE II

The blood gas-electrolyte controls of this invention are prepared by conventional manufacturing techniques using readily available materials. A typical control within the contemplation of this invention is prepared by simply combining in appropriate relative proportions, buffer, electrolytes, foaming agent and other standard auxiliary reagents and chemicals; the pH and concentration of dissolved carbon dioxide thereof being adjusted to the appropriate value, depending on the natures, the control, an aliquot thereof placed in a sealable receptacle: the receptacle flushed with gas: and the receptacle sealed so as to create a headspace above control fluids which is occupied by the gas. Albumin may be added if a protein matrix is desired. Glycine is added to bind a portion of the calcium to provide a total calcium value that reflects normal values for Level II and abnormal values for Levels I and III. The glycine also prevents precipitation of the remaining ionized calcium.

The performance of a Diamond Sensor Gem 6 Blood Gas-Electrolyte monitor is verified using a blood gas-electrolyte control. The controls are comprised of three levels: normal and two abnormal conditions. Level one, an abnormal control, having low electrolyte levels, acidosis pH and gas levels which represent respiratory, acidosis, level two, normal parameters and level three, high levels of electrolytes, alkalosis pH and gas levels which represent respiratory alkalosis, were formed in the presence of the biological buffer N-2-hydroxyethylpiperazine-N'-2'ethanesulfonic acid. This buffer was selected due to the temperature effect demonstrated by the buffer. The temperature coefficient (change in pKa per degree C.=0.014), enables the control to indicate a malfunction of the instrument temperature regulation. The material is packaged in glass ampules which have been flushed with the appropriate gases. This ampule must be shaken prior to use in a blood gas-electrolyte analyzer. The shaking equilibrates the gas with the liquid and also creates a foam layer. The foam layer will protect the solution from contamination with room air gases for 4 minutes after opening the ampule.

TABLE II

| | LEVEL 1 | LEVEL 2 | LEVEL 3 |
|---|---|---|---|
| NaCL (mMol/L) | 41 | 48 | 79 |
| $CaCl_2$ (mMol/L) | 2.1 | 2.9 | 3.4 |
| KCL (mMol/L) | 2.5 | 4.2 | 6.8 |
| Glycine (mMol/L) | 639 | 599 | 532 |
| $O_2$ (mmHg) | 40 | 100 | 150 |
| $CO_2$ (mmHg) | 60 | 40 | 13 |
| HEPES (mMol/L) | 50 | 50 | 50 |
| pH (37° C.) | 7.16 | 7.4 | 7.6 |
| $Na^+$ (mMol/L) | 120 | 138 | 150 |
| $K^+$ (mMol/L) | 2.5 | 4 | 6.8 |
| $Ca^{2+}$ (mMol/L) | 0.9 | 1.15 | 1.5 |
| Total Ca (mg/dl) | 8.5 | 11.5 | 13.5 |
| $CL^-$ (mMol/L) | 86 | 102 | 116 |
| Ionic Strength mMol/L | 160 | 160 | 160 |

Table II lists the composition of the three levels of the blood gas-electrolyte control solution together with concentrations and pH values.

The calibrator and control solutions are currently used to calibrate and control the Diamond Sensor Systems GEM-6 blood gas electrolyte monitor. The two level calibrator solutions are used to perform two calibration points on the instrumentation. The calibration points at 37 C. are:

| PARAMETER* | LOW CALIBRATOR | HIGH CALIBRATOR |
|---|---|---|
| pH | 6.9 ± 0.02 | 7.4 ± 0.02 |
| $pCO_2$ | 65 mmHg ± 3.0 | 35 mmHg ± 3.0 |
| $pO_2$ | 0 mmHg ± 5.0 | 115 ± 5.0 |
| $K^+$ | 2.0 mM/L ± 0.3 | 6.0 mM/L ± 0.3 |
| $Ca^{++}$ | 0.2 mM/L ± 0.1 | 2.0 mM/L ± 0.1 |

*Stated values are at atmospheric pressure, temperature coefficient of pH = −.01 pH unit/C.

EXAMPLE III

The control formulations by typical blood gas electrolyte instrumentation. Table III shows the results of some of these tests.

TABLE III

Typical Values Expected Aqueous Blood Gas/Electrolyte Control

| Parameter | Level | Instrument | Mean | Expected Range | 1SD |
|---|---|---|---|---|---|
| pH | I | Il 1303 | 7.16 | 7.14–7.28 | 0.002 |
| pH | I | Corning 178 | 7.17 | 7.15–7.19 | 0.006 |
| pH | I | NOVA Stat | 7.15 | 7.13–7.17 | 0.001 |
| pH | II | Il 1303 | 7.39 | 7.37–7.41 | 0.004 |
| pH | II | Corning 178 | 7.41 | 7.39–7.43 | 0.002 |
| pH | II | NOVA Stat | 7.40 | 7.36–7.42 | 0.006 |
| pH | III | Il 1303 | 7.63 | 7.62–7.65 | 0.002 |
| pH | III | Corning 178 | 7.63 | 7.61–7.65 | 0.001 |
| pH | III | NOVA Stat | 7.64 | 7.62–7.66 | 0.003 |
| $pCO_2$ mmHg | I | Il 1303 | 64 | 59–69 | 1.0 |
| $pCO_2$ mmHg | I | Corning 178 | 67 | 62–72 | 2.8 |
| $pCO_2$ mmHg | I | NOVA Stat | 66 | 61–71 | 1.0 |
| $pCO_2$ mmHg | II | Il 1303 | 36 | 32–40 | 0.2 |
| $pCO_2$ mmHg | II | Corning 178 | 36 | 32–40 | 0.4 |
| $pCO_2$ mmHg | II | NOVA Stat | 36 | 32–40 | 0.8 |
| $pCO_2$ mmHg | III | Il 1303 | 11.0 | 9–13 | 0.1 |
| $pCO_2$ mmHg | III | Corning 178 | 8.0 | 6–10 | 0.1 |
| $pCO_2$ mmHg | III | NOVA Stat | 11.0 | 9–13 | 0.1 |
| $pO_2$ mmHg | I | Il 1303 | 42 | 34–50 | 1.4 |
| $pO_2$ mmHg | I | Corning 178 | 41 | 33–49 | 2.0 |
| $pO_2$ mmHg | I | NOVA Stat | 42 | 34–50 | 1.3 |
| $pO_2$ mmHg | II | Il 1303 | 104 | 96–112 | 2.0 |
| $pO_2$ mmHg | II | Corning 178 | 106 | 98–114 | 3.0 |
| $pO_2$ mmHg | II | NOVA Stat | 102 | 94–110 | 3.9 |
| $pO_2$ mmHg | III | Il 1303 | 180 | 172–188 | 2.5 |
| $pO_2$ mmHg | III | Corning 178 | 183 | 175–191 | 3.1 |
| $pO_2$ mmHg | III | NOVA Stat | 189 | 183–199 | 2.5 |
| Sodium mM/L | III | NOVA 6 | 139 | 134–144 | 0.8 |
| Sodium mM/L | III | NOVA Stat | 141 | 136–146 | 1.0 |
| Sodium mM/L | III | NOVA 10 | 144 | 139–149 | 1.0 |
| Potassium mM/L | I | NOVA 6 | 2.4 | 2.1–2.7 | 0.1 |
| Potassium mM/L | I | NOVA Stat | 2.5 | 2.2–2.8 | 0.1 |
| Potassium mM/L | I | NOVA 10 | 2.4 | 2.1–2.7 | 0.1 |
| Potassium mM/L | II | NOVA 6 | 4.0 | 3.7–4.3 | 0.1 |
| Potassium mM/L | II | NOVA Stat | 3.8 | 3.5–4.1 | 0.1 |
| Potassium mM/L | II | NOVA 10 | 3.8 | 3.5–4.1 | 0.1 |
| Potassium mM/L | III | NOVA 6 | 6.4 | 6.1–6.7 | 0.1 |
| Potassium mM/L | III | NOVA Stat | 6.9 | 6.6–7.2 | 0.1 |
| Potassium mM/L | III | NOVA 10 | 0.65 | 6.2–6.8 | 0.1 |
| iCa mM/L | I | NOVA 6 | 0.8 | 0.6–1.0 | 0.1 |
| iCa mM/L | I | NOVA Stat | 0.8 | 0.6–1.0 | 0.1 |
| iCa mM/L | II | NOVA 6 | 1.1 | 0.9–1.3 | 0.1 |
| iCa mM/L | II | NOVA Stat | 1.1 | 0.9–1.3 | 0.1 |
| iCa mM/L | III | NOVA 6 | 1.6 | 1.4–1.8 | 0.1 |
| iCa mM/L | III | NOVA Stat | 1.6 | 1.4–1.8 | 0.1 |
| Chloride mM/L | I | NOVA Stat | 96 | 93–99 | 0.4 |
| Chloride mM/L | I | NOVA 10 | 96 | 93–99 | 0.2 |
| Chloride mM/L | II | NOVA Stat | 108 | 104–112 | 1.0 |
| Chloride mM/L | II | NOVA 10 | 108 | 104–112 | 0.1 |
| Chloride mM/L | III | NOVA Stat | 124 | 120–128 | 0.3 |
| Chloride mM/L | III | NOVA 10 | 124 | 121–129 | 0.1 |
| Total Ca mg/L | I | NOVA 10 | 0.9 | 0.7–1.1 | 0.2 |
| Total Ca mg/L | II | NOVA 10 | 1.0 | 0.8–2.2 | 0.2 |
| Total Ca mg/L | III | NOVA 10 | 1.8 | 1.6–2.0 | 0.2 |
| Lithium mM/L | I | Corning Flame | 0.6 | 0.4–0.8 | 0.3 |
| Lithium mM/L | II | Corning Flame | 1.7 | 1.5–1.1 | 0.3 |
| Lithium mM/L | III | Corning Flame | 3.0 | 2.8–3.2 | 0.3 |

While these calibrating and control systems are particularly advantageous in biological fluid analysis systems such as Diamond Sensor Systems GEM-6 it will be apparent that other biological fluid analysis systems can use the presently described calibrating and control solutions. Therefore, while particular embodiments of the invention have been shown and described, various modifications will be apparent to those skilled in the art and therefore is not intended that the invention be limited to the disclosed embodiments or to details thereof and departures may be made there from within the spirit and scope of the invention.

What is claimed is:

1. A method of making a control for use with a blood-gas-electrolyte chemical analyzer, the method comprising:
   (a) employing an aqueous solution of electrolytes comprising sodium ions, potassium ions, calcium ions, and chloride ions;
   (b) controlling the level of gaseous oxygen in said aqueous solution to maintain a $pO_2$ from 40 to 200 mmHg;
   (c) adding bicarbonate ions to said aqueous solution to provide $CO_2$;
   (d) adding a buffering system to said aqueous solution to provide a pH of between about 6.9 and 7.8; and
   (e) adding a stabilizer for calcium ions to said aqueous solution in order to prevent the precipitation of calcium ions as calcium carbonate.

2. The method of claim 1 wherein the stabilizer for calcium ions is selected from the group consisting of sulfate ions and glycine.

3. The method of claim 2 wherein the electrolytes in said aqueous solution further comprise lithium ions.

4. The method of claim 2 wherein the buffering system comprises a temperature sensitive buffer.

5. The method of claim 4 wherein the temperature sensitive buffer is selected from the group of buffers consisting of N-2-hydroxyethylpiperazine-N'2-ethanesulfonic acid and 3-(N-morpholino) propane sulfonic acid.

6. The method of claim 2 wherein the aqueous solution is stored in a gas tight container.

7. The method of claim 6 wherein the aqueous solution further comprises a foaming agent wherein the concentration of the foaming agent is sufficient to form a foam layer when the solution is shaken and provides an open container stability up to approximately four minutes.

8. The method of claim 7 wherein aliquots of the aqueous solution are prepared with different levels of the electrolytes, gaseous oxygen and bicarbonate ion and each aliquot is stored in a separate gas tight container.

* * * * *